United States Patent
Braun

(10) Patent No.: US 6,723,708 B2
(45) Date of Patent: Apr. 20, 2004

(54) USE OF LITHIUM (LI+) FOR THE PREPARATION OF A COMPOSITION FOR TRANSFECTION OF A POLYNUCLEOTIDE INTO A CELL AND COMPOSITIONS USEFUL IN GENE THERAPY

(75) Inventor: Serge Braun, Dorlisheim (FR)

(73) Assignee: Transgene S.A., Strasbourg (FR)

( * ) Notice: Subject to any disclaimer, the term of this patent is extended or adjusted under 35 U.S.C. 154(b) by 37 days.

(21) Appl. No.: 09/741,997

(22) Filed: Dec. 22, 2000

(65) Prior Publication Data

US 2001/0018426 A1 Aug. 30, 2001

Related U.S. Application Data

(60) Provisional application No. 60/186,676, filed on Mar. 3, 2000.

(30) Foreign Application Priority Data

Dec. 12, 1999 (EP) .............................. 99403310

(51) Int. Cl.$^7$ ................................ A61K 48/00

(52) U.S. Cl. ..................... 514/44; 435/320.1; 435/325; 435/455

(58) Field of Search ............................ 435/69.1, 320.1, 435/325, 455, 91.4, 315; 514/44

(56) References Cited

U.S. PATENT DOCUMENTS

| 4,711,955 | A | 12/1987 | Ward et al. |
| 5,525,711 | A | 6/1996 | Hawkins et al. |
| 5,595,897 | A | 1/1997 | Midoux et al. |
| 6,372,722 | B1 * | 4/2002 | Bennett et al. |
| 6,387,695 | B1 * | 5/2002 | Evans et al. |

FOREIGN PATENT DOCUMENTS

| EP | 0 302 175 | 2/1989 |
| FR | 2 719316 | 11/1995 |
| WO | WO 95/24221 | 3/1995 |
| WO | WO 96/02655 | 7/1995 |

OTHER PUBLICATIONS

Wagner et al. "Delivery of Drugs, Proteins and Genes Into Cells Using Transferrin as a Ligand for Receptor–Mediated Endocytosis" *Advanced Drug Delivery Reviews* vol. 14 (1994) p. 113 135.

Haensler and Sozoka, Jr., "Polyamidoamine Cascade Polymers Mediate Efficient Transfection of Cells in Culture". *Biocenjugate Chem.*, vol. 4 (1993) p. 372 379.

Felgner et al. "Cationic Lipid–Mediated Delivery of Polynucleotides". *Methods*, vol. 5 (1993) p. 67 75.

Gao and Huang "A Novel Cationic Liposome Reagent for Efficient Transaction of Mammalian Cells", *Biochemical and Biophysical Research Comunications*, vol. 179, No. 1 (1991) p. 280 285.

Tsan et al. "Lung Specific Direct in Vivo Gene Transfer with Recombinant Plasmid DNA" *Am. J. Physiol.* vol. 268, No. 6 (1995) p. L1052 1056.

Davis et al, "Plasmid DNA is Superior to Viral Vectors for Direct Gene Transfer into Adult Mouse Skeletal Muscle" *Human Gene Therapy*, vol. 4 (1993) p. 733–740.

Evans & Robbins, "Gene Therapy for Arthritis", Birkhaiser, Boston (1990) p. 320 43 NLM 1994 C 762.

Behr, Jean–Paul et al, "Efficient Gene Transfer into Mammalian Primary Endocrine Cells with Lipopolyamine–Coated DNA", Proc. Natl. Acad. Sci., vol. 86, pp. 6982–6986, Sep. 1989.

Davis, Heather L. et al, "Direct Gene Transfer into Skeletal Muscle In Vivo: Factors Affecting Efficiency of Transfer and Stability of Expression", Human Gene Therapy 4:151–159 (1993).

Felgner, P.L. et al, "Cationic Liposome–Mediated Transfection", Nature vol. 337, Jan. 26, 1989.

Felgner, P.L. et al, "Lipofection: A Highly Efficient, Lipid–Mediated DNA–Transfection Procedure", Proc. Natl. Acad. Sci., vol. 84, pp. 7413–7417, Nov. 1987.

Hickman, M. Anne et al, "Gene Expression Following Direct Injection of DNA into Liver", Human Gene Therapy 5:14777–1483, Dec. 1994.

Lenox, Robert H. et al, "Neurobiology of Lithium: An Update", J. Clin. Psychiatry 1998; 59 (suppl 6), pp. 37–47.

McLachlan, G. et al, "Evaluation in Vitro and in Vivo of Cationic Liposome–Expression Construct Complexes for Cystic Fibrosis Gene Therapy", Gene Therapy (1995) 2, 614–622.

Meyer, K.B. et al, "Intratracheal Gene Delivery to the Mouse Airway: Characterization of Plasmid DNA expression and Pharmacokinetics", Gene Therapy (1995) 2, 450–460.

Perales, Jose C. et al, "An evaluation of Receptor–Mediated Gene Transfer Using Synthetic DNA–Ligand Complexes", Eur. J. Biochem, 226, 255–266 (1994).

Raz, Eyal et al, "Intradermal Gene Immunization: The Possible Role of DNA Uptake in the Induction of Cellular Immunity to Viruses", Proc. Natl. Acad. Sci., vol. 91, pp. 9519–9523, Sep. 1994.

Schwartz, B et al, "Gene Transfer by Naked DNA into Adult Mouse Brain", Gene Therapy (1996) 3, 405–411.

Sikes, Michael L., "In Vivo Gene Transfer into Rabbit Thyroid Follicular Cells by Direct DNA Injection", Human Gene Therapy 5:837–844 (1994).

Soares, Jair C. et al, "The Lithium Ion: A Foundation for Psychopharmacological Specificity", Neuropsychopharmocology 1998, vol. 19, No. 3.

(List continued on next page.)

Primary Examiner—Dave T. Nguyen
(74) Attorney, Agent, or Firm—Burns, Doane, Swecker & Mathis, L.L.P.

(57) ABSTRACT

Described is the use of lithium (Li$^+$) for the preparation of a therapeutic composition for the introduction of a polynucleotide into a cell.

11 Claims, 1 Drawing Sheet

OTHER PUBLICATIONS

Figure 1:
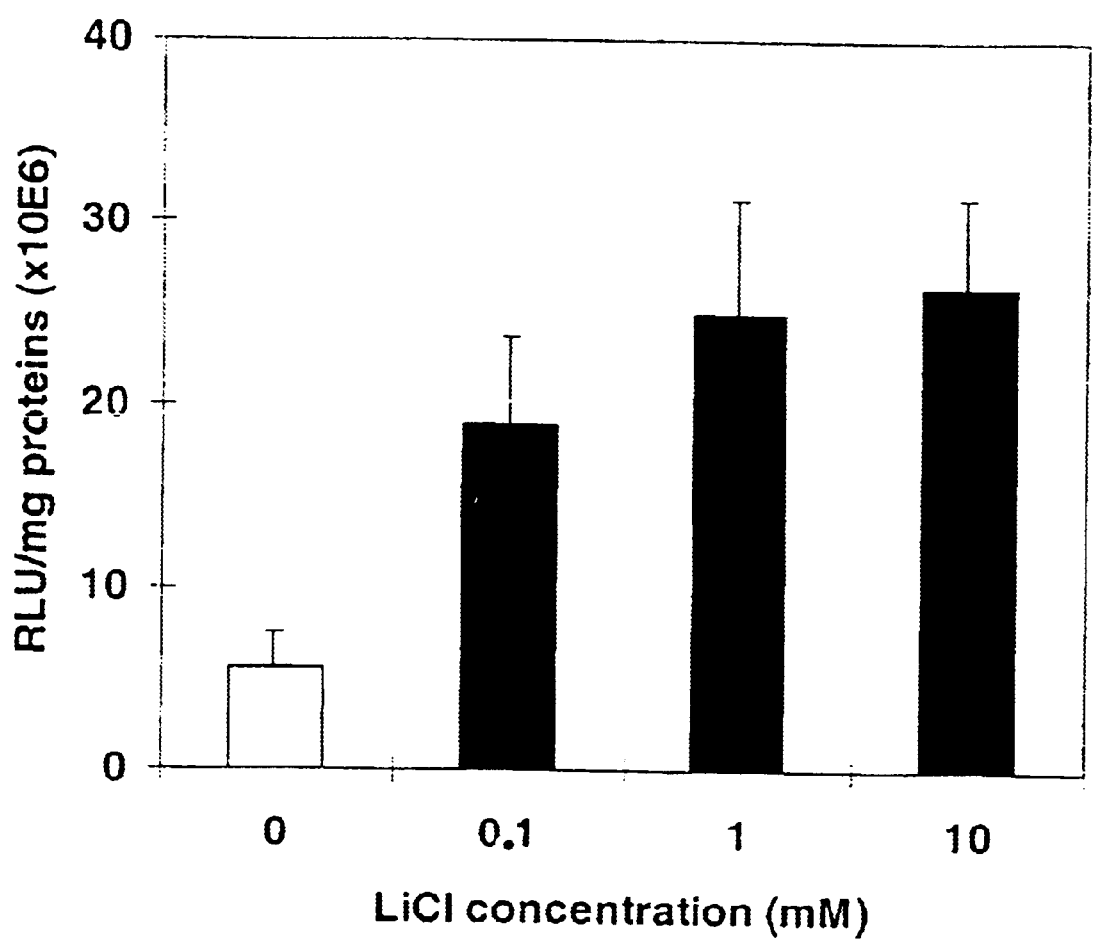

Wolff, Jon A. et al, "Direct Gene Transfer into Mouse Muscle in Vivo", Science, vol. 247, pp. 1465–1468, 1990.

Manthorpe et al: "Gene Therapy by Intramuscular Injection of Plasmid DNA: Studies on Firefly Luciferase Gene Expression in Mice", Human Gene Therapy, vol. 4, Aug. 1993, p. 419–431 XP000199375.

Wolff et al: "Conditions Affecting Direct Gene Transfer into Rodent Muscle in Vivo", Biotechniques. vol. 11, No. 4, Nov. 1991, p. 474 485 XP000973460.

Wells et al: "Evaluation of Plasmid DNA for In Vivo Gene Therapy: Factors Affecting the Number of Transfected Fibers", J. Pharmaceutical Sci., vol. 87, No. 6, Jun. 1998, p. 763–768 XP002099635.

Yamakawa et al: "Intact Cell Transformation of Saccaromyces Cerevisiae Bypolyethylene Glycol", Agric. Biol. Chem., vol. 49, No. 3, Mar. 1985. pp. 869–871. XP000995689.

* cited by examiner

USE OF LITHIUM (LI+) FOR THE PREPARATION OF A COMPOSITION FOR TRANSFECTION OF A POLYNUCLEOTIDE INTO A CELL AND COMPOSITIONS USEFUL IN GENE THERAPY

This application claims priority under 35 U.S.C. §§119 (e) to Provisional Application No. 60/186,676 filed in the United States on Mar. 3, 2000; the entire content of which is hereby incorporated by reference.

The present invention relates to the use of lithium ($Li^+$) for the preparation of a composition for improving transfection or transduction of a polynucleotide into a cell. Such a composition is useful in gene therapy, vaccination, and any therapeutic or prophylactic situation in which a gene-based product is administered to cells in vivo.

Gene therapy has generally been conceived as principally applicable to heritable deficiency diseases (cystic fibrosis, dystrophies, haemophilias, etc.) where permanent cure may be effected by introducing a functional gene. However, a much larger group of diseases, notably acquired diseases (cancer, AIDS, multiple sclerosis, etc.) might be treatable by transiently engineering host cells to produce beneficial proteins.

Applications are, for example, the treatment of muscular dystrophies or of cystic fibrosis. The genes of Duchenne/Becker muscular dystrophy and cystic fibrosis have been identified and encode polypeptides termed dystrophin and cystic fibrosis transmembrane conductance regulator (CFTR), respectively. Direct expression of these genes within, respectively, the muscle or lung cells of patients should contribute to a significant amelioration of the symptoms by expression of the functional polypeptide in targeted tissues. Moreover, in cystic fibrosis studies have suggested that one would need to achieve expression of the CFTR gene product in only about 5% of lung epithelial cells in order to significantly improve the pulmonary symptoms.

Another application of gene therapy is vaccination. In this regard, the immunogenic product encoded by the polynucleotide introduced in cells of a vertebrate may be expressed and secreted or be presented by said cells in the context of the major histocompatibility antigens, thereby eliciting an immune response against the expressed immunogen. Functional polynucleotides can be introduced into cells by a variety of techniques resulting in either transient expression of the gene of interest, referred to as transient transfection when said polynucleotide consists in plasmid derived polynucleotide, transduction when said polynucleotide consists in a viral derived polynucleotide, or permanent transformation of the host cells resulting from incorporation of the polynucleotide into the host genome.

Successful gene therapy depends on the efficient delivery to and expression of genetic information within the cells of a living organism. Most delivery mechanisms used to date involve viral vectors, especially adeno- and retroviral vectors. Viruses have developed diverse and highly sophisticated mechanisms to achieve this goal including crossing of the cellular membrane, escape from lysosomal degradation, delivery of their genome to the nucleus and, consequently, have been used in many gene delivery applications in vaccination or gene therapy applied to humans.

Besides, non-viral delivery systems have been developed which are based on receptor-mediated mechanisms (Perales et al., Eur. J. Biochem. 226 (1994), 255–266; Wagner et al., Advanced Drug Delivery Reviews 14 (1994), 113–135), on polymer-mediated transfection such as polyamidoamine (Haensler and Szoka, Bioconjugate Chem. 4 (1993), 372–379), dendritic polymer (WO 95/24221), polyethylene imine or polypropylene imine (WO 96/02655), polylysine (U.S. Pat. No. 5,595,897 or FR 2 719 316) or on lipid-mediated transfection (Felgner et al., Nature 337 (1989), 387–388) such as DOTMA (Felgner et al., Proc. Natl. Acad. Sci. USA 84 (1987), 7413–7417), DOGS or Transfectam™ (Behr et al., Proc. Natl. Acad. Sci. USA 86 (1989), 6982–6986), DMRIE or DORIE (Felgner et al., Methods 5 (1993), 67–75), DC-CHOL (Gao and Huang, BBRC 179 (1991), 280–285), DOTAPTM (McLachlan et al., Gene Therapy 2 (1995), 674–622) or Lipofectamine™. These systems present potential advantages with respect to large-scale production, safety, targeting of transfectable cells, low immunogenicity and the capacity to deliver large fragments of DNA. Nevertheless their efficiency in vivo is still limited.

Finally, in 1990, Wolff et al. (Science 247 (1990), 1465–1468) have shown that injection of naked RNA or DNA, i.e. without a special delivery system, directly into mouse skeletal muscle results in expression of reporter genes within the muscle cells. This technique for transfecting cells offers the advantage of simplicity and experiments have been conducted that support the usefulness of this system for the delivery to the lung (Tsan et al., Am. J. Physiol. 268 (1995), L1052–L1056; Meyer et al., Gene Therapy 2 (1995), 450–460), brain (Schwartz et al., Gene Therapy 3 (1996), 405–411) joints (Evans and Roddins, Gene therapy for arthritis; In Wolff (ed) Gene therapeutics: Methods and Applications of direct Gene Transfer. Birkhaiser. Boston (1990), 320–343), thyroid (Sikes et al., Human Gen. Ther. 5 (1994), 837–844), skin (Raz et al., Proc. Natl. Acad. Sci. USA 91 (1994), 9519–9523) and liver (Hickman et al., Hum. Gene Ther. 5 (1994), 1477–1483). Nevertheless, Davis et al. (Human Gene Therapy 4 (1993), 151–159 and Human Mol. Genet. 4 (1993), 733–740) observed a large variability of expression of naked DNA injected into skeletal muscle in vivo which would be insufficient for the treatment of primary myopathies, for example. The authors propose solutions in order to obtain an improvement of the efficiency of gene transfer by preinjecting muscles with a relatively large volume of hypertonic sucrose or with toxins, for example cardiotoxin isolated from snake, in order to stimulate regeneration of muscles. Nevertheless, these methods, although promising, would not be applicable for human treatment.

Thus, the available delivery methods are not satisfactory in terms of safety or efficiency for their implementation in in vivo gene therapy.

Therefore, the technical problem underlying the present invention is the provision of improved methods and means for the delivery of nucleic acid molecules, either naked or combined with special delivery facilitating agents such as cationic lipid, polymer, or viral protein, in gene therapy.

This technical problem is solved by the provision of the embodiments as defined in the claims.

Thus, the present invention relates to the use of lithium ($Li^+$) for the preparation of a composition for transferring a polynucleotide into a cell. It was surprisingly found that the specific addition of lithium when transferring a polynucleotide into vertebrate cells, and in particular into vertebrate tissue, leads to a dramatic improvement of the transfer efficiency. Thus, the present invention preferably relates to the use of lithium ($Li^+$) for the preparation of a pharmaceutical composition for an improved transfer of a polynucleotide into a cell.

The term "polynucleotide" within the present invention is intended to designate both naked and non-naked nucleic acid. A "nucleic acid" may be a DNA or RNA, single or double stranded, linear or circular, natural or synthetic, modified or not (see U.S. Pat. No. 5,525,711, U.S. Pat. No. 4,711,955 or EP-A 302 175 for modification examples). It may be, inter alia, a genomic DNA, a genomic RNA, a cDNA, an mRNA, an antisense RNA, a ribosomal RNA, a ribozyme, a transfer RNA or DNA encoding such RNAs. The nucleic acid may be in the form of a plasmid or linear nucleic acid which contains at least one expressible sequence that can generate a polypeptide, a ribozyme, an antisense RNA or another molecule of interest upon delivery to a cell. The nucleic acid can also be an oligonucleotide (i.e. a nucleic acid having a short size of less than 100 bp) which is to be delivered to the cell, e.g., for antisense or ribozyme functions. According to the invention, said nucleic acid can be either naked or non-naked. "Naked" means that said nucleic acid, irrespective of its nature (DNA or RNA), its size, its form (single/double stranded, circular/linear, . . . ), is defined as being free from association with transfection-facilitating viral particles, liposomal formulations, charged lipids or polymers and precipitating agent (Wolff et al., Science 247 (1990), 1465–1468; EP 465529). On the opposite, "non-naked" means that said nucleic acid may be associated (i) with viral polypeptides forming what is usually called a virus (adenovirus, retrovirus, poxvirus, etc . . . ) or forming a complex where the nucleic acid while being associated with is not included into a viral element such as viral capsid (see U.S. Pat. No. 5,928,944 and WO 9521259), (ii) with a liposomal formulation, a charged compound (charged lipids or polymers for example ) or with any component which can participate in the transferring uptake of the nucleic acid into the cells (see Ledley, Human Gene Therapy 6 (1995), 1129–1144 for a review). Charged compounds to which the polynucleotide is associated are preferably cationic lipids, especially those disclosed in WO 98/34910 or EP 901463. Preferably, the nucleic acid is in the form of plasmid DNA and the polynucleotide is a naked plasmid DNA. A wide range of plasmids is commercially available and well known by one skilled in the art. These available plasmids are easily modified by the molecular biology techniques (Sambrook et al, 1989, Laboratory Manual, Cold Spring Harbor Laboratory Press, Cold Spring Harbor, N.Y.). Plasmids derived from pBR322 (Gibco BRL), pUC (Gibco BRL), pBluescript (Stratagene), pREP4, pCEP4 (Invitrogen) and also p Poly (Lathe et al., 1987, Gene 57, 193–201) are illustrative of these modifications.

If the nucleic acid contains the proper genetic information, it will direct the synthesis of relatively large amounts of the encoded polypeptide. When the polynucleotide delivered to the cells contains a nucleic acid encoding an immunizing polypeptide, the use according to the invention can be applied to achieve improved and effective immunity against infectious agents, including intracellular viruses, and also against tumor cells. The genetic informations necessary for expression by a target cell comprise all the elements required for transcription of said DNA into mRNA and for translation of mRNA into polypeptide. Transcriptional promoters suitable for use in various vertebrate systems are widely described in litterature. For example, suitable promoters include viral promoters like RSV, MPSV, SV40, CMV or 7.5 k, vaccinia promoter, inducible promoters, etc. The nucleic acid can also include intron sequences, targeting sequences, transport sequences, sequences involved in replication or integration. Said sequences have been reported in the literature and can be readily obtained by those skilled in the art. The nucleic acid or the polynucleotide can also be modified in order to be stabilized with specific components as spermine.

According to the invention, "introduction or transfer" means that the polynucleotide is transferred into the cell and is located, at the end of the process, inside said cell or within or on its membrane. It is also called "transfection" or "transduction" depending of the nature of the polynucleotide; "transfection" is dedicated to design transfer of polynucleotides which do not comprise viral element such as capsid or viral polypeptide, and "transduction" designate transfer of viruses. Those terminologies are usual in the technical field of the invention.

The term "improved transfer" in the scope of the present invention means, in this regard, a more efficient transfer of a polynucleotide by cells when lithium ($Li^+$) is present compared to an introduction performed without lithium. This can be determined by comparing the amount of the polynucleotide taken up without the use of lithium and comparing this amount with the amount taken up by the cells when using lithium under the same experimental conditions. Preferably, the improved transfer can be determined by a higher amount of expression of the polynucleotide transferred into the cells when using lithium ($Li^+$) in comparison to a situation where no lithium ($Li^+$) is used.

The composition prepared according to the use of the present invention can be used for transfection of a polynucleotide into a cell in vivo or ex vivo. In this regard, ex vivo means that the cells into which the polynucleotide is transfected are not located in an organism, but may be transferred into an organism after transfection.

The term "gene therapy method" is preferably understood as a method for the transfer of a polynucleotide into cells in vivo. "Gene therapy" in particular concerns the case where the gene product is expressed in a target tissue as well as the case where the gene product is excreted, especially into the blood stream.

Lithium ($Li^+$) has been previously described as a first-line approach in the treatment of acute mania and the prophylactic management of manic-depressive illness. It is able to stabilize recurrent depression associated with unipolar disorder, and is efficient in the treatment of refractory major depressive disorder in the presence of an antidepressant (Soares J C; Gershon S, 1998 Neuropsychopharmacology, 19:167182; Lenox R H et al. 1998, J Clin Psychiatry, 59 Suppl 6:37–47)

The term "lithium ($Li^+$)" as used herein, means the monovalent cation of lithium. Such a product is commercially available associated with one or several biologically acceptable anions, such as, for example, bromide, chloride, fluoride, sulfate, phosphate, nitrate, niobate, petaphosphate, tantalate, manganese oxide, molybdate, oxide, peroxide, silicate, iodide, tetrachloroaluminate, tetrachlorogallate, tetrafluoroborate, etc . . . (see Aldrich catalogue, 1996/1997, for example). According to a preferred embodiment, said lithium ($Li^+$) is associated with chloride (LiCl). In a preferred embodiment the amount of lithium in the compositions prepared according to the use of the present invention ranges between about 0.1 to about 100 mM, preferably from about 0.1 to about 10 mM of lithium, and still preferably is 10 mM. This concentration may also be adapted by those skilled in the art in particular cases where lithium concentration can be affected. For example, when the composition further comprises chelating agent, such as EDTA or EGTA, it would be preferable to improve the lithium concentration in order to compensate for lithium depletion due to chelation. This can occur when the polynucleotide has been previously prepared in a buffer such as TE (Tris-EDTA).

In a preferred embodiment the composition prepared according to the use of the present invention is in a form for administration into a vertebrate tissue. These tissues include those of muscle, skin, brain, lung, liver, spleen, bone marrow, thymus, heart, lymph, bone, cartilage, pancreas, kidney, gall bladder, stomach, intestine, testis, ovary, uterus, rectum, nervous system, eye, gland, connective tissue, blood, tumor etc. Cells where the improved transfer of a foreign polynucleotide would be obtained are those found in each of the listed target tissues (muscular cells, airway cells, hematopofetic cells, etc.). The administration may be made by intradermal, subdermal, intravenous, intramuscular, intranasal, intracerebral, intratracheal, intraarterial, intraperitoneal, intravesical, intrapleural, intracoronary or intratumoral route, by injection with a syringe or other devices. Transdermal administration is also contemplated, as are inhalation or aerosol administration. Site of administration and site of transfer of the polynucleotide can be identical or different. In a preferred embodiment, the therapeutic composition prepared according to the invention is for the transfer into muscle cells, more preferably, by intramuscular injection routes or intravascular route. Referring to the latter, the administration method can be advantageously improved by combining injection in a afferent and/or efferent vessel with increases of permeability of said vessel. In a special embodiment, said increases is obtained by increasing hydrostatic pressure (i.e. by obstructing outflow and/or inflow), osmotic pressure (with hypertonic solution) and/or introducing a biologically-active molecule (e.g. histamine into administered composition) (see WO 98/58542).

In another preferred embodiment, the invention provides the use of lithium for the preparation of a therapeutic composition for improving transfer of a polynucleotide into a cell wherein said therapeutic composition is administered independently from a second administration consisting in administration of a composition containing at least one polynucleotide. According to the present invention, the first administration can be done prior to, concurrently with or subsequent to the second administration, and vice-versa. The therapeutic composition administration and second administration can be performed by different or identical delivery routes (systemic delivery and targeted delivery, or targeted deliveries for example). In a preferred embodiment, each should be done into the same target tissue and most preferably by injection.

In a further preferred embodiment of the use according to the present invention, the composition further comprises at least one polynucleotide. In a particularly preferred embodiment, the polynucleotide which is contained in the composition, contains and is capable of functionally expressing a encoding nucleic acid sequence in said cell.

In general, the concentration of the polynucleotide in the composition is from about 0.01 mM to about 1 M, and in a preferred embodiment is from about 0.1 mM to 10 mM. According to the invention, the polynucleotide can be homologous or heterologous to the target cells into which it is introduced. Advantageously said polynucleotide encodes all or part of a polypeptide, especially a therapeutic or prophylactic polypeptide giving to the composition a therapeutic or prophylactic property. A polypeptide is understood to be any translational product of a polynucleotide regardless of size, and whether glycosylated or not, and includes peptides and proteins. Therapeutic polypeptides include as a primary example those polypeptides that can compensate for defective or deficient proteins in an animal or human organism, or those that act through toxic effects to limit or remove harmful cells from the body. They can also be immunity conferring polypeptides which act as endogenous immunogens to provoke a humoral or cellular response, or both. Examples of polypeptides encoded by the polynucleotide are enzymes, hormones, cytokines, membrane receptors, structural polypeptides, transport polypeptides, adhesines, ligands, transcription factors, traduction factors, replication factors, stabilization factors, antibodies, more especially CFTR, dystrophin, factors Vil or IX, E6 or E7 from HPV, MUC1, BRCA1, interferons, interleukin (IL-2, IL-4, IL-6, IL-7, IL-12, GM-CSF (Granulocyte Macrophage Colony Stimulating Factor), the tk gene from Herpes Simplex type 1 virus (HSV-1), p53 or VEGF. The polynucleotide can also code for an antibody. In this regard, antibody encompasses whole immunoglobulins of any class, chimeric antibodies and hybrid antibodies with dual or multiple antigen or epitope specificities, and fragments, such as $F(ab)_2$, Fab', Fab including hybrid fragments and anti-idiotypes (U.S. Pat. No. 4,699,880).

In a further preferred embodiment the composition further comprises at least one component selected from the group consisting of chloroquine, protic compounds such as propylene glycol, polyethylene glycol, glycerol, ethanol, 1-methyl L-2-pyrrolidone or derivatives thereof, aprotic compounds such as dimethylsulfoxide (DMSO), diethylsulfoxide, di-n-propylsulfoxide, dimethylsulfone, sulfolane, dimethylformamide, dimethylacetamide, tetramethylurea, acetonitrile or derivatives. Said composition can also comprises at least one component selected from the group consisting of cytokines, especially interleukin-10 (IL-10), and nuclease inhibitors such as, for example, actin G.

In another preferred embodiment the composition prepared according to the use of the invention can be used in a method for the therapeutic treatment of humans or animals. In this particular case, the composition may also comprise a pharmaceutically suitable injectable carrier or diluent (for examples, see Remington's Pharmaceutical Sciences, $16^{th}$ ed. 1980, Mack Publishing Co). The carrier or diluent is preferably isotonic, hypotonic or weakly hypertonic and has a relatively low ionic strength, such as provided by a sucrose solution. Furthermore, it may contain any relevant solvents, aqueous or partly aqueous liquid carriers comprising sterile, pyrogen-free water, dispersion media, coatings, and equivalents, or diluents (e.g;, Tris-HCl, acetate, phosphate), emulsifiers, solubilizers or adjuvants. The pH of the pharmaceutical preparation is suitably adjusted and buffered in order to be useful in in vivo applications. It may be prepared either as a liquid solution or as a solid form (e.g.lyophilized) which is suspended in a solution prior to administration.

In another aspect the present invention also relates to a process for transferring a polynucleotide into cells wherein said process comprises contacting said cells with a composition prepared according to the use of the invention before, simultaneously or after contacting them with the polynucleotide. This process may be applied by direct administration of said composition to cells of the animal in vivo. According to the practice of the invention, targeted "cells" and "in vivo administration route" are defined as above described. "Targeted cells" are those where polynucleotide uptake and expression occur; they are not necessarily located into the injected tissue (site of administration). In a special embodiment, administration is done into vessel and polynucleotide transfection or infection occurs at a proximal or distal site, for example in organ or tissue, such as lung, muscle, liver, kidney; heart, . . . .

Preferably, muscle is used as a site for the delivery and expression of a polynucleotide in a number of therapeutic applications because animals have a proportionately large muscle mass which is conveniently accessed by direct injection through the skin. Accordingly, in a preferred case, the invention concerns a process for introducing a polynucleotide, preferably in naked form, into muscle cells in vivo, comprising the steps of administering in vivo at least a polynucleotide and lithium, preferably intramuscularly, whereby the polynucleotide is directly administered into muscle cells of the tissue or intravascularly, whereby the polynucleotide is administered into efferent and/or afferent muscle vessel. The polynucleotide may encode a therapeutic polypeptide that is expressed by the muscle cells and eventually secreted into the blood stream after the contacting step to provide therapy to the vertebrate. Similarly, it may encode an immunogenic polypeptide that is expressed by the muscle cells after the contacting step and which generates an immune response, thereby immunizing the vertebrate. One important aspect of the invention is a process for the treatment of muscular dystrophy wherein said polynucleotide operatively codes for dystrophin. Preferably, the composition is directly administered into the muscle tissue.

Finally, the present invention relates to the use of lithium ($Li^+$) for improving transfer of a polynucleotide into a cell, either in vitro (or ex vivo, see above) or in vivo.

The invention has been described in an illustrative manner, and it is to be understood that the terminology which has been used is intended to be in the nature of words of description rather than of limitation. Obviously, many modifications and variations of the present invention are possible in light of the above teachings. It is therefore to be understood that within the scope of the claims, the invention may be practiced otherwise than as specifically described.

All of the above cited disclosures of patents, publications and database entries are specifically incorporated herein by reference in their entirety to the same extent as if each such individual patent, publication or entry were specifically and individually indicated to be incorporated by reference.

FIG. 1: shows the effect of LiCl on intramuscular transfection of pTG11033. Luciferase activity of mouse right and left tibialis anterior muscles measured 7 days after injection with 25 μg plasmid added with NaCl 0.9% buffer (Control, NaCl) or with 0.1 to 10 mM of LiCl. Bars are means of RLU (Relative Light Unit) per minute per mg protein +/− s.e.m. of 6 mesures.

The following examples illustrate the invention.

MATERIAL AND METHODS

The following materials and methods are used in the examples.

1. Intramuscular Administration of Plasmid/Divalent Ion Composition

Plasmid DNA (pTG11033: CMV promoter, β-globin intron, luciferase cassette—WO 98/34910) was prepared according to Bischoff et al., Analytical Biochemistry 254 (1997), 69–81. Prior to intramuscular injection the tested molecules were mixed with the plasmid DNA preparation. 25 μg of plasmid DNA were injected per muscle into 5 to 10 week-old C57BL/10 mice. The 2 tibialis anterior (right and left) muscles were injected (each muscle was considered as a sample). Furthermore, for each condition, both the lowest and highest luciferase acitvity values were omitted, which means number of sample per condition=(2×number of mice per condition)−2.

2. Muscle Biopsies and Luciferase Measurement

One week after injection of the composition, the mice were killed and the tibialis anterior muscles were retrieved and frozen. Luciferase activity was quantified on whole muscle extracts using a conventional measurement kit (Luciferase Assay System, Promega). Briefly, muscles were ground separately and diluted in 200 μl of reporter lysis buffer (Promega). 10 μl-samples were placed in 96 well-plates and mixed with 100 μl of substrate. Luciferase activity was expressed as number of RLU emitted per minute, per mg of protein.

3. Protein Determination

Protein was measured on 10 μl samples using a VCA Protein Assay kit (Pierce).

EXAMPLE 1

LiCl increases transfection in vivo (intramuscular administration of plasmid DNA in mice)

In this example, the stock solution of plasmid pTG11033 was prepared in TE buffer (Tris 10 mM—EDTA 1 mM) at a nucleic acid concentration of 1 μg/pl.

Stock solution of LiCl was prepared in water at a concentration of 1 M.

Four C57Bl/10 mice were injected per condition into the right and left tibialis anterior muscle with different compositions comprising pTG11033 (25 μg/muscle) and various concentrations of lithium chloride (0.1, 1, 10 mM). The control experiment is performed according to the same condition except that no monovalent ion is added and that 5 μl of NaCl 0.9% is added. The injected volume was 30 μl.

The results are presented in FIG. 1. They show that LiCl allowed an increase of luciferase activity in the injected muscles (around 5 times in the present example).

What is claimed is:

1. A method for improving the transfer of a polynucleotide into a cell comprising contacting a cell with 0.1 to about 10 mM of lithium chloride to improve the transfer of a polynucleotide into the cell.

2. The method according to claim 1, wherein the cells are simultaneously or subsequently contacted with polynucleotide.

3. The method according to claim 1, wherein said tissue cell is muscle.

4. The method according to claim 1, wherein the administration of lithium chloride is performed independently from a second administration of a composition containing at least one polynucleotide to the same cell.

5. The method according to claim 4, wherein the administration of lithium chloride is performed prior to said second administration.

6. The method according to claim 4, wherein the polynucleotide contains a gene and in capable of functionally expressing said gene in said cell.

7. The method according to claim 4, wherein said polynucleotide is naked nucleic acid.

8. The method according to claim 4, wherein said polynucleotide is a non-naked nucleic acid.

9. The method according to claim 4, wherein the polynucleotide is administered alone with a pharmaceutically acceptable amount and is present in a concentration from about 0.01 mM to about 1 mM.

10. The method according to claim 4, wherein said cells are contacted with lithium chloride before, simultaneously and subsequently to contact with the polynucleotide.

11. The method according to claim 10, wherein the cells are simultaneously contacted with the lithium chloride and the polynucleotide.

* * * * *